(12) United States Patent
Knothe Tate

(10) Patent No.: US 12,310,875 B2
(45) Date of Patent: May 27, 2025

(54) SUBSTRATE

(71) Applicant: Bioconix Pty Ltd, Wentworth Falls (AU)

(72) Inventor: Melissa L. Knothe Tate, New South Wales (AU)

(73) Assignee: BIOCONIX PTY LTD, New South Wales (AU)

( * ) Notice: Subject to any disclaimer, the term of this patent is extended or adjusted under 35 U.S.C. 154(b) by 1727 days.

(21) Appl. No.: 14/912,260

(22) PCT Filed: Aug. 15, 2014

(86) PCT No.: PCT/AU2014/000813
§ 371 (c)(1),
(2) Date: Feb. 16, 2016

(87) PCT Pub. No.: WO2015/021503
PCT Pub. Date: Feb. 19, 2015

(65) Prior Publication Data
US 2016/0193069 A1 Jul. 7, 2016

Related U.S. Application Data

(60) Provisional application No. 61/866,795, filed on Aug. 16, 2013.

(30) Foreign Application Priority Data

Nov. 14, 2013 (AU) .................. 2013904409

(51) Int. Cl.
A61F 5/058 (2006.01)
A61F 5/01 (2006.01)
(Continued)

(52) U.S. Cl.
CPC ............ *A61F 5/058* (2013.01); *A61F 5/0104* (2013.01); *A61F 13/01038* (2024.01);
(Continued)

(58) Field of Classification Search
CPC ...... A61F 5/058; A61F 5/0104; A61F 5/0109; A61F 5/0102; A61F 5/01; A61F 5/05816;
(Continued)

(56) References Cited

U.S. PATENT DOCUMENTS 2,448,782 A 9/1948 Davis
4,012,459 A 3/1977 Takeya et al.
(Continued)

FOREIGN PATENT DOCUMENTS

DE 8528007 11/1982
EP 0548609 A1 6/1993
(Continued)

OTHER PUBLICATIONS

Knit definition,Dictionary.com,https:/Avww.dictionary.com/browse/knit (Year: 2020).*
(Continued)

*Primary Examiner* — Ophelia A Hawthorne
*Assistant Examiner* — Gina McCarthy
(74) *Attorney, Agent, or Firm* — Tarolli, Sundheim, Covell & Tummino LLP

(57) ABSTRACT

A substrate that can be applied to a user's body part having a region of temporally-controlled elasticity that transitions between a first state and a second state when activated, wherein the first state is more relaxed than the second state, and the substrate can at least partially revert from the second state to the first state over an extended time period resulting from the temporally-controlled elasticity of the substrate, (Continued)

and wherein the substrate can apply a treatment/mechanical force to the body part, as the substrate transitions from the second state to the first state.

20 Claims, 7 Drawing Sheets

(51) Int. Cl.
  *A61F 13/00*    (2024.01)
  *A61F 13/01*    (2024.01)
  *A61F 13/08*    (2006.01)
  *A61F 13/10*    (2006.01)

(52) U.S. Cl.
  CPC ............ *A61F 13/08* (2013.01); *A61F 13/101* (2013.01); *A61F 2013/00131* (2013.01); *A61F 2013/0028* (2013.01)

(58) Field of Classification Search
  CPC .............. A61F 5/05825; A61F 5/05833; A61F 13/00038; A61F 13/08; A61F 13/085; A61F 13/101; A61F 13/102; A61F 13/107; A61F 13/00; A61F 2013/00119; A61F 2013/00131; A61F 2013/00136; A61F 2013/0014; A61F 2013/00144; A61F 2013/00148; A61F 2013/0028; A61F 2013/00272; A61F 15/006; A61F 13/0206; A61H 9/0078; A41B 9/001; D03D 1/00

See application file for complete search history.

(56) References Cited

U.S. PATENT DOCUMENTS

| | | | |
|---|---|---|---|
| 4,442,057 A | 4/1984 | Brody | |
| 4,527,402 A | 7/1985 | Swallow et al. | |
| 4,665,909 A * | 5/1987 | Trainor | A61F 15/006 602/76 |
| 4,727,868 A * | 3/1988 | Szycher | A61F 13/0206 66/193 |
| 5,843,523 A | 12/1998 | Mazza et al. | |
| 6,315,009 B1 | 11/2001 | Jayaraman et al. | |
| 7,490,634 B2 * | 2/2009 | Resendez | D03D 1/00 139/423 |
| 8,491,514 B2 | 7/2013 | Creighton et al. | |
| 2004/0016043 A1 * | 1/2004 | Uno | A41B 9/001 2/400 |
| 2007/0215836 A1 | 9/2007 | Van Bruggen et al. | |
| 2009/0076432 A1 | 3/2009 | Winkler | |
| 2009/0099497 A1 | 4/2009 | Jung et al. | |
| 2009/0234265 A1 * | 9/2009 | Reid, Jr. | A61H 9/0078 602/76 |
| 2009/0299255 A1 | 12/2009 | Kazala, Jr. et al. | |
| 2012/0226214 A1 | 9/2012 | Gurtner et al. | |
| 2013/0254971 A1 | 10/2013 | Galluzzo et al. | |
| 2013/0296763 A1 | 11/2013 | Farrow et al. | |
| 2013/0303957 A1 * | 11/2013 | Bauerfeind | A61H 1/008 602/76 |

FOREIGN PATENT DOCUMENTS

| | | |
|---|---|---|
| FR | 2169161 A1 | 9/1973 |
| GB | 1077533 A | 8/1967 |
| GB | 1139846 A | 1/1969 |
| WO | 9203107 A1 | 3/1992 |
| WO | 92003107 | 3/1992 |
| WO | 9513038 A1 | 5/1995 |
| WO | 0249558 A2 | 6/2002 |
| WO | 2005106087 A1 | 11/2005 |
| WO | 2008112242 A2 | 9/2008 |
| WO | 2010132950 A1 | 11/2010 |
| WO | 2012045427 A1 | 4/2012 |
| WO | 2012150440 A2 | 11/2012 |
| WO | 2013063554 A1 | 5/2013 |
| WO | 2013127875 | 9/2013 |
| WO | 2013138394 A1 | 9/2013 |
| WO | 2013149985 A1 | 10/2013 |
| WO | 2014052318 A1 | 4/2014 |
| WO | 2014057285 A1 | 4/2014 |

OTHER PUBLICATIONS

Woven definition,Dictionary.com,https:/Avww.dictionary.com/browse/woven (Year: 2020).*
International Preliminary Report on Patentability for Application No. PCT/AU2014/000813 dated Dec. 14, 2015 (15 pages).
International Search Report and Written Opinion for Application No. PCT/AU2014/000813 dated Nov. 3, 2014 (72 pages).
Applicant: Bioconix PTY Ltd, "A Substrate"; Australian Application No. 2021209209; Australian Examination Report dated Jul. 15, 2022; 8 pgs.

* cited by examiner

Carbon nanotubes
nanotube reference length scale:
length $\ell$ and diameter $\phi$
$\ell : \phi$ up to $132 \times 10^6$
diameter length scale: nm "Hollow hairs"
natural biodegradable or polymer
polar bear hair as reference ($\phi \sim 4\text{-}100$ um)

Titanium "hooklets"

ously, the substrate may be activated by the
SUBSTRATE

FIELD OF INVENTION

The present invention relates to a substrate that can be applied to a user's body part.

BACKGROUND OF THE INVENTION

Current methods for supporting or immobilising injured external body parts (such as the shoulder or knee) or internal body parts (such as skin, muscle, bone, ligaments, tendons or fasciae) often involve the use of substrates such as strapping and bandages. These include externally applied tapes and splints and internally applied sutures or clamps or staples, all of which are fixed to the body part at the time of application.

Substrates such as compression garments (or bandages) may also utilise pressure to rehabilitate a body part.

For example, women diagnosed with breast cancer may suffer from upper limb lymphoedema, a chronic condition resulting from the accumulation of lymph fluid associated with damaged lymph nodes from cancer surgery and/or radiotherapy.

Compression is the most effective option for managing lymphoedema and patients are often required to wear a compression garment (or bandages) to prevent recurrence of swelling. However, most compression garments comprise heavy-knit fabrics, making them difficult to don/doff, as well as being uncomfortable and ill-fitting.

These garments typically slacken over time resulting in a loss of pressure. As a result, these garments have to be unfastened from the body part and re-tightened in order to maintain pressure on the body part.

Additionally, the force provided by these supports to hold the body part cannot usually be varied because, in use, these supports are fixed or mounted onto the body part using attachment points, such as sutures, that form an immobile connection between the support and the body part.

Consequently, excessive movement, such as overstretching, may cause the tissue in the vicinity of the attachment points, which is often weaker than the support, to tear.

It is desirable to provide a substrate that can support and maintain pressure on a body part. Preferably, the substrate also reduces damage to the body part.

SUMMARY OF THE INVENTION

In one form of the present invention, there is provided a substrate that can be applied to a user's body part having a region of temporally-controlled elasticity that transitions between a first state and a second state when activated, wherein the first state is more relaxed than the second state, and the substrate can at least partially revert from the second state to the first state over an extended time period resulting from the temporally-controlled elasticity of the substrate, and wherein the substrate can apply a treatment/mechanical force to the body part, as the substrate transitions from the second state to the first state.

In this specification, temporally-controlled elasticity refers to an ability to control the elasticity of the substrate over time.

In this specification, the term "fibre" or variations thereof including "fibres" embrace staple fibres including natural or modified fibres, filaments including synthetic filaments and fibrils, including synthetic fibrils. A body part includes any part of a human body including external body parts such as hands, shoulders and feet, and internal body parts such as tissues, skin, muscle, bone, ligaments, tendons, fasciae and blood vessels. Reference to a body part can further include inanimate body parts from sports, exercise and leisure equipment, vehicular docking or transport systems, safety lines for construction and rescue operations, and micro-docking or tensioning systems.

Advantageously, the substrate may be activated by the natural movements of the body part to generate dynamic pressure that can transition the substrate from the first state to the second state. This effect can be optimised or maximised by employing weaving algorithms, using spatial and temporal patterns of elasticity which includes elastic and inelastic patterns, to form the substrate.

The substrate may be applied externally for rehabilitating hand, foot and joint injuries. Alternatively, the substrate may be applied internally to allow connection, support and/or ligation of tissue.

When used externally, the substrate provides support to injured areas or weakness of a body part. When used internally, the substrate enables connection, support and/or ligation of tissues, including blood vessels, ligaments, muscles and bones.

Activation of the substrate may include applying an external force to the substrate. The external force may be stored as potential energy, whereby part of the potential energy is converted to a mechanical force (e.g. pressure) that is applied to the body part as the substrate reverts from the second state to the first state. Part of the potential energy stored in the substrate may also be converted into kinetic energy as the substrate reverts from the second state to the first state. The kinetic energy may manifest itself as peristaltic movement of the substrate which in turn generates a corresponding peristaltic movement of the body part.

The first state may be a relaxed state, for instance, when the substrate is not under tension.

The substrate may also be under some tension in the first state. However, the internal (stored) energy of the substrate in the first state is less than the internal (stored) energy of the substrate in the second state.

Activation may be induced by extending a body part to stretch the substrate which, in turn, triggers a pressure wave (also known as passive activation).

Alternatively, activation may be induced by external stimulus, such as for example, ultrasound, vibration, heat, radiofrequency or ultraviolet light (also known as directed activation).

The force applied to the body part by the substrate may vary, such as reduce or increase, as the substrate reverts from the second state to the first state.

The gradient (i.e. the change in pressure over time) of the force is a function of the temporally-controlled elasticity of the substrate. In turn, the temporally-controlled elasticity of the substrate is a function of the internal energy of the substrate.

The transition of the substrate from the second state to the first state may generate a dynamic pressure gradient to a body part. This may be used to augment compression and lymph drainage over time. For example, as the substrate moves from the second state to the first state, the substrate may cause peristalsis of the body part.

The substrate may move from the second state to the first state upon removal of a force exerted on the substrate via any one of elongation or shortening of the material, or relaxation or stiffening of the material.

The substrate may allow targeted harnessing or transfer of displacements and/or forces due to movement of the body to induce a change in the substrate structure, which in turn, causes a change in the function of the substrate. For example, the substrate may exert a pressure gradient and provide support to a body part as the substrate transitions from the second state to the first state.

Temporally-controlled elasticity controls the pressure gradient exerted by the substrate on the body part over time when the substrate reverts from the second state to first state.

The pressure gradient may be constant, increasing or decreasing. The pressure gradient may be changing and include any one or a combination of a constant, increasing or decreasing pressure gradients.

In the first state, the pressure on the body part is substantially reduced or removed.

The substrate may possess spatially-controlled elasticity, whereby different regions of the substrate have different elasticity. Suitably, different regions of the substrate possess temporally-controlled elasticity. The substrate may possess spatially-controlled and temporally-controlled elasticity.

The temporally-controlled elasticity of the substrate may, in a first example, be provided by a manner in which the substrate is woven using threads (also known as fibres), each including an assembly of fibrils. The threads may be arranged (for example, woven) in different directions to form the substrate such that the threads move frictionally relative to one another causing the transition from the first state to the second state to occur over an extended time period. In other words, the threads interact in a manner such that relative movement of the threads is restricted.

The relative movement of the fibres may include either one or a combination of: (i) relative movement of the fibres within the threads; or (ii) relative movement of the fibres in different threads (i.e. threads in different directions).

Each thread may have different elasticity. Suitably, at least one thread has temporally-controlled elasticity.

In this example, when the threads interact with each other when transitioning from the first state to the second state, the elasticity of the threads and the friction between the threads contribute to the restricted movement of the threads relative to each other.

The substrate may be anisotropic. The substrate may be woven such that applying a force to the substrate causes a transversal reaction on the substrate. For example, if the substrate is in the form of a sheet, applying a force along the length of the substrate would cause a breadth-wise expansion or contraction of the substrate. In another example, if the substrate is in the form of a sleeve, applying an axial force to the substrate would cause a circumferential expansion or contraction of the substrate.

The substrate may comprise threads having varying elasticity and temporally-varying elasticity.

In a second example, the temporally-controlled elasticity of the substrate is provided by the substrate including at least one thread possessing elasticity that varies along the length of the thread. The substrate may include at least one thread possessing elasticity that varies within the cross-section of the thread. The substrate may include two or more threads possessing different elasticity.

In a third example, the temporally-controlled elasticity of the substrate may be provided by a combination of the first and second examples.

The threads may be formed by spinning different fibrils together. Each fibril may possess elasticity that varies along the length of the fibril and/or elasticity that varies within the cross-section of the fibril. The threads may be processed to allow cross-linking between the threads and/or the fibrils.

The fibrils may have a diameter ranging from 1-1500 μm.

The threads may be arranged in specific patterns to effect higher order functional characteristics that cannot be achieved with a homogenous weave, for example, spatially-controlled spring back (tension) and spatially-controlled pressure upon application of exogenous force, displacement, or other forms of energy application.

These threads may comprise any one or a combination of biopolymers such as collagen, silk, elastin, or linear elastic core yarns polymers, or synthetic polymers such as polytetrafluoroethylene.

These threads may possess energy dissipation properties. Examples of such threads are collagen, silk, and polytetrafluoroethylene. Alternatively, these threads may possess energy return properties (i.e. elasticity). Examples of such threads are elastin and linear elastic core yarns.

These threads may exhibit gradients in these properties along their length. These threads may also be arranged in space to achieve specific gradients in the substrate.

The substrate may be woven using at least two threads having different stiffness, thinning and swelling properties.

At least one thread may vary in composition along its length.

The substrate may comprise a degradable material. This allows the substrate to be removed from a body after a time period without manual intervention. For example, the substrate may be used to support a sutured blood vessel, and degrade from the blood vessel over time.

At least a region of the substrate may be cloaked/covered to control the regions of the substrate that exhibit temporally-controlled elasticity.

The substrate may include a plurality of connectors for attaching the substrate to a body part, tissue, or another substrate.

The connectors may reduce relative movement of the substrate to the body part, tissue, or another substrate.

The connectors may provide targeted tightening and/or immobilisation of a substrate to facilitate healing of a body part.

The connectors may allow the substrate to connect to a body part with controlled tension banding and/or controlled creep and/or relaxation behaviour.

The plurality of connectors may be projections, such as hooks or nanotubes, which provide a non-permanent grip to hold the substrate to a body part.

The plurality of connectors may provide a grip that has a predetermined detachment load and/or direction to hold the substrate to the body part. The detachment load is less than the load required to damage the body part. This minimises damage to the body part. For example, the connectors detach from the body part to prevent flesh on the body part from tearing when a force exceeding the detachment load is applied to the substrate.

The connectors may be oriented in more than one direction to provide a multi-directional grip onto the body part to reduce the likelihood of the substrate detaching from the body part when subjected to a force.

The plurality of connectors may provide multiple (redundant) non-permanent attachment points for connecting the substrate to a body part, particularly, on the surface of the body part. Each of these attachment points may have a predetermined detachment load and/or direction.

The temporally-controlled elasticity of the substrate allows the number of attachment points between the substrate and the surface to be varied over time as the substrate moves between the second and first states. For example, some connectors may detach from the body part when a predetermined force magnitude and/or direction is exceeded during the movement of the substrate from the first state to the second state. On the other hand, the connectors may attach or re-attach to the body part when the substrate moves from the second state to the first state.

This may provide a more constant gripping force between the substrate and the body part to reduce the likelihood of the connector damaging the body part. This is in contrast to fixed connectors such as sutures or clamps. For example, excessive movement may cause a fixed connector, such as a suture, to tear the surface it is attached to. In contrast, non-permanent connectors may detach from the body part when a predetermined force magnitude and/or direction on the connectors is exceeded. This reduces the likelihood of the body part on which the connector is attached to from tearing.

The connectors may be used to deliver biologic and/or pharmaceutical agents at attachment points, such as for example, to reduce inflammation, direct cell growth and extracellular matrix deposition. This may strengthen natural bonding at the attachment points.

The connectors may be hollow to deliver biologic and/or pharmaceutical agents through wicking of pharmaceuticals and/or biologics. The hollow connectors may be used to inject these agents and/or establish conduits between the connector and a body part.

The substrate may be used to connect body parts that require tension banding and/or controlled creep and/or relaxation behaviour at multiple length scales. For example, surgical reconstruction, such as small calibre vessel/nerve ligation, or tissue graft connectors.

The formed substrate may comprise sub-weave bands in biaxial weave structure.

The substrate may include a conduit, heating element or electrode to provide a pressure and/or thermoelectric gradient to the substrate.

The substrate may be an open weave textile. This allows air flow to a body part supported by the substrate to increase cooling of the body part and increase comfort. An open weave textile may also improve removal of moisture from the body part.

Suitably, the substrate is a biaxial braided sleeve whose circumference constricts with an increase in the length of the sleeve. The sleeve allows the generation of a directed pressure gradient along the length of the sleeve when the sleeve is stretched.

The sleeve may comprise multiple layers of the substrate, wherein each substrate has different temporally-controlled elasticity. Suitably, the sleeve is transitionable between a first state and a second state by stretching the sleeve.

The sleeve may be moved to the second state by for example, by natural movement of a body part, without having to remove and tighten the sleeve.

In another form of the invention, there is provided a method of forming a substrate having a region of temporally-controlled elasticity that transitions between a first state and a second state when activated, and the substrate reverts from the second state to the first state over an extended time period, and wherein the substrate can apply a force to a body part as the substrate transitions from the second state to the first state.

The method of forming the substrate may use a Jacquard loom, which have an advantage of producing fine, attractive weaves.

The method includes forming a substrate comprising sub-weave bands in biaxial weave structure.

Specific patterns of elasticity (stiffness) and creep or relaxation, within the weave bands, from fibre to fibre, and within fibres, may provide specific patterns of spatially and temporally varying pressure gradients when the body part is moved.

In another form of the present invention, there is provided a method of forming a substrate having at least one region of temporally-controlled elasticity, including the steps of:
  (a) spinning fibres to form anisotropic threads; and
  (b) assembling the anisotropic threads to form the substrate.

The assembly step may be a step of weaving and/or knitting.

The spinning step and/or the assembly step may be computer controlled. The spinning step and/or the assembly step may also be recursive. In one form of the invention, the spinning step and/or the assembly step employs weaving algorithms, using spatial and temporal patterns of (in-) elasticity, to create dynamic pressure that harnesses the arm's natural movements.

The method of forming a substrate having at least one region of temporally-controlled elasticity may include a step of weaving threads having varying composition and/or elasticity along their length into the substrate.

The incorporation of threads having varying composition along their length may impart spatially-controlled elasticity to the substrate.

The assembly step may include orienting the threads in space relative to each other. Alternatively, the assembly step may include orienting gradients of threads relative to each other. This allows the behavior of the substrate in the spatial domain to be engineered recursively.

The assembly step may include orienting threads having different elasticity along their length according to a predetermined algorithm. This controls the behavior of the substrate as the substrate transitions between the first state to the second state.

Recursive engineering or recursive weaving uses a top-down approach to solving a complex problem (e.g. creating a multidimensional, complex architectural weave) by breaking the problem down into a sequence of steps using computational algorithms. This allows each desired property in space and time to be engineered virtually into the algorithm and subsequently achieved physically through computer-controlled weaving.

Controlling the gradients of the threads also allows higher order functionality of the substrate to be achieved.

In another form of the present invention, there is provided a sleeve for fitting over a body part comprising a substrate having at least one region of temporally-controlled elasticity, wherein the substrate is transitionable between an first state and an second state by moving the sleeve.

The sleeve may comprise multiple layers of the substrate, wherein each substrate has a different temporally-controlled elasticity. Suitably, the substrate is transitionable between an first state and an second state by stretching the sleeve.

The substrate remains in the second state by for example, by natural movement of a body part, without having to remove and tighten the sleeve. In contrast, conventional compression bandages may slacken over time and have to be unwrapped and re-tightening to maintain pressure over a body part.

BRIEF DESCRIPTION OF DRAWINGS

A preferred embodiment of the present invention is hereinafter described by way of example only, with reference to the accompanying drawings, wherein.

DETAILED DESCRIPTION

Figure 1A:
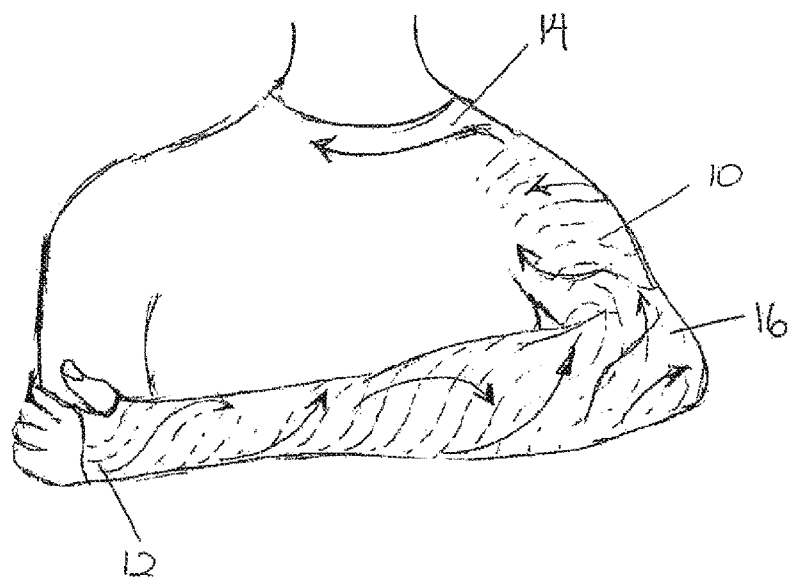
FIG. 1A illustrates a substrate for supporting an arm/shoulder according to one form of the present invention.

One form of the substrate as defined by the invention is marked as 10 in FIG. 1A.

The substrate 10 is in the form of a biaxial braided sleeve having a fingerless glove portion 12, and a collar portion 14. The substrate 16 has temporally-controlled elasticity. Another form of the biaxial braided sleeve is shown in FIG. 1C.

The substrate 16 is assembled by recursive weaving involving computer-controlled weaving of anisotropic threads (or fibres) that vary in composition along their length. These threads are, in turn, formed by computer-controlled spinning of fibrils to form the anisotropic threads.

Figures 7A, 7B:
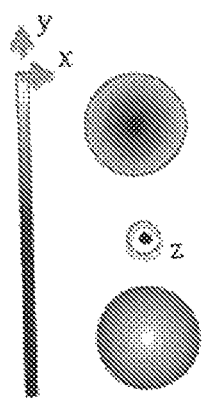
FIGS. 7A and 7B illustrate the different anisotropic fibres used for forming a substrate according to the present invention.

Threads that possess elasticity that varies along the length of the thread (FIG. 7A), elasticity that varies within the cross-section of the thread (FIG. 7B), and/or threads possessing different elasticity may be used to assemble the substrate.

Figure 10A:
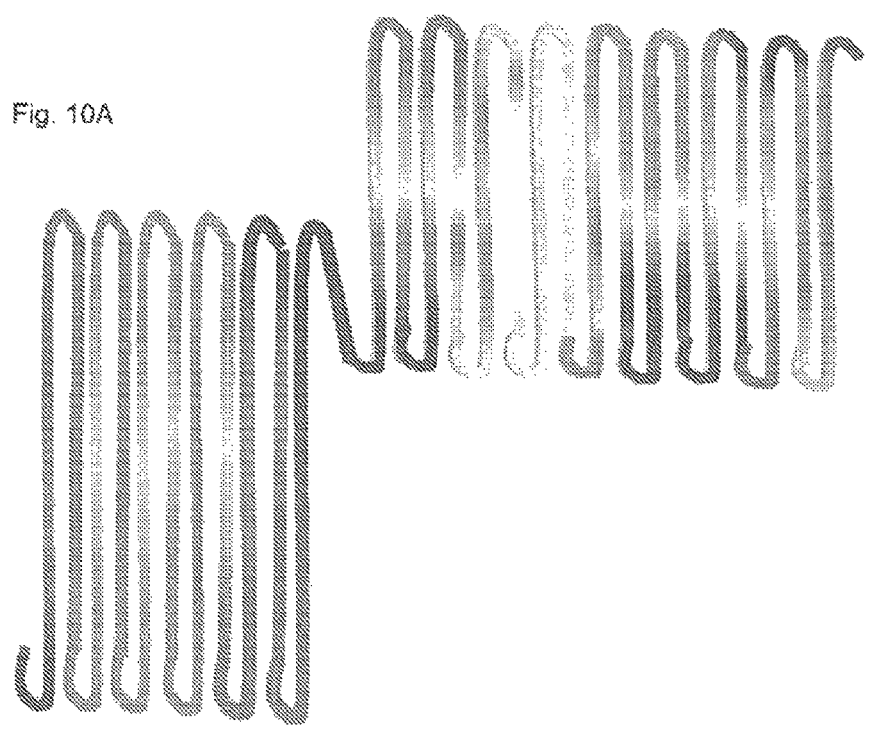
FIGS. 10A-C illustrates the steps for forming a textile according to the present invention using a thread having varying elasticity along its length.

FIG. 10A illustrates an anisotropic thread formed by spinning fibrils together. The shading gradient on the thread denote the varying elasticity along the length of the thread.

Weaving algorithms, using spatial and temporal patterns of (in-)elasticity, are used to harnesses a body part's, such as an arm's, natural movements for the substrate to create dynamic pressure.

During the weaving process, the anisotropic threads are oriented relative to each other to align or contact specific regions of one thread to another thread. The behavior of the substrate in response to a force is provided by the specific arrangement of the threads relative to each other.

Figure 8A:
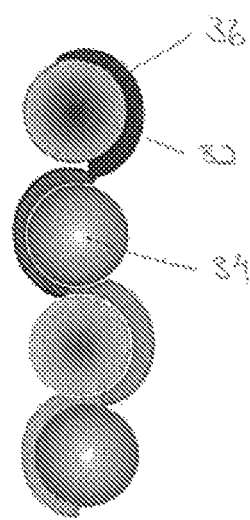
FIG. 8A illustrates a 2-D weave for forming a substrate according to the present invention.
Figure 8B:
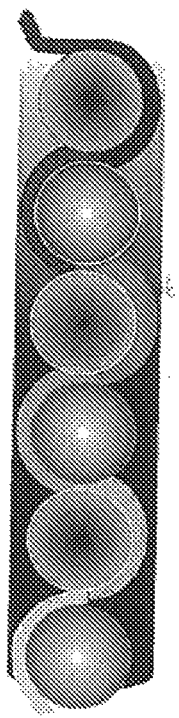
FIG. 8B illustrates a 3-D weave for forming a substrate according to the present invention.
Figure 10B:
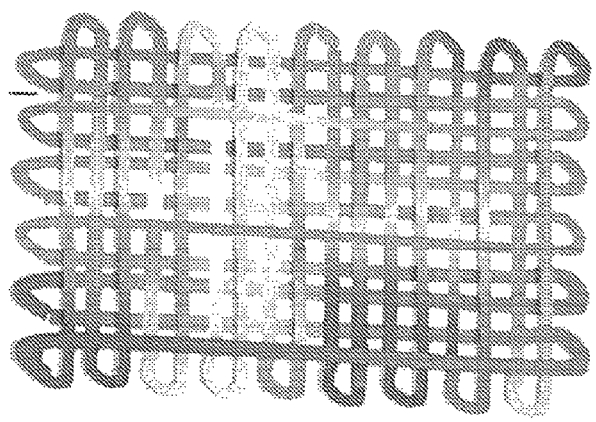

The threads may form a 2-D weave/band wherein parallel threads (32 and 34 of FIG. 8A) are woven together using a thread (36 of FIG. 8A) that runs transversely to threads 32 and 34. FIG. 10B illustrates a substrate formed by weaving at least two threads of FIG. 10A. The threads may form a 3-D weave/band wherein the threads 32-36 are woven in a high viscosity medium to form a coated weave/band. Weaving in the medium makes it possible to use hydrodynamic shuttling (injection and ejection through a liquid) as well as to use the medium itself as a constituent of the composite weave, for example, after the fibre weaving is complete, the medium itself can be 'solidified' (e.g. through a chemical process or application of external energy) around the weave, providing a higher order composite structure with expanded mechanical and biophysical properties. The medium can also be manipulated to exhibit properties that vary spatially and temporally, for example, through anisotropic curing and/or polymerisation.

Figure 9:
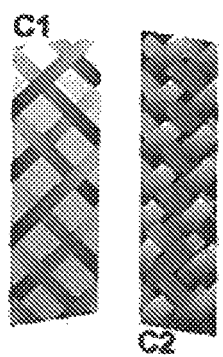
FIG. 9 illustrates interwoven 2-D bands according to the present invention.

Higher order weaves may also be formed, such as for example, interweaving the 2-D bands to form a complex architecture whereby the bands can slide between/on each other. The open weave textile in FIGS. 9C1 and 9C2 allows air flow to the arm and illustrates the movement of the 2-D bands relative to each other.

Figure 10C:
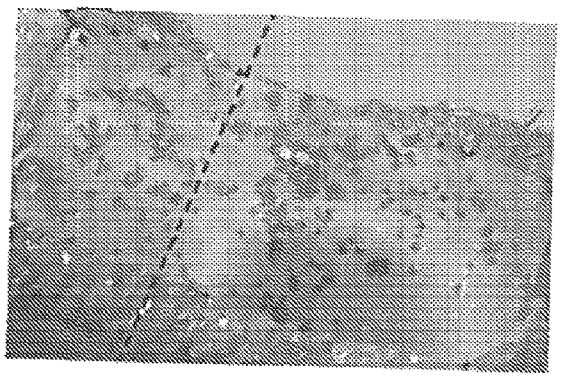

Another higher order weave is illustrated in FIG. 10C. The shading on the textile in FIG. 10C illustrates its varying spatial and temporal properties.

The threads in the woven substrate are arranged in different directions such that the fibres slide frictionally relative to one another when transitioning from the first state to the second state over a time period. During the transition, the friction between the threads and the different elasticity of the threads restricts the relative movement of the fibres. This imparts various stretching and compressive properties to the substrate.

Figure 1B:
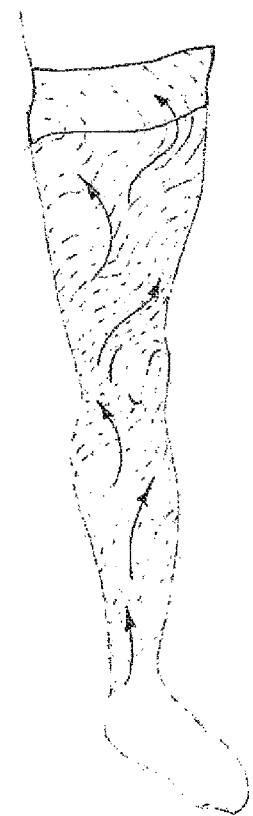
FIG. 1B illustrates a substrate for supporting a leg/foot according to another form of the present invention.
Figure 1C:
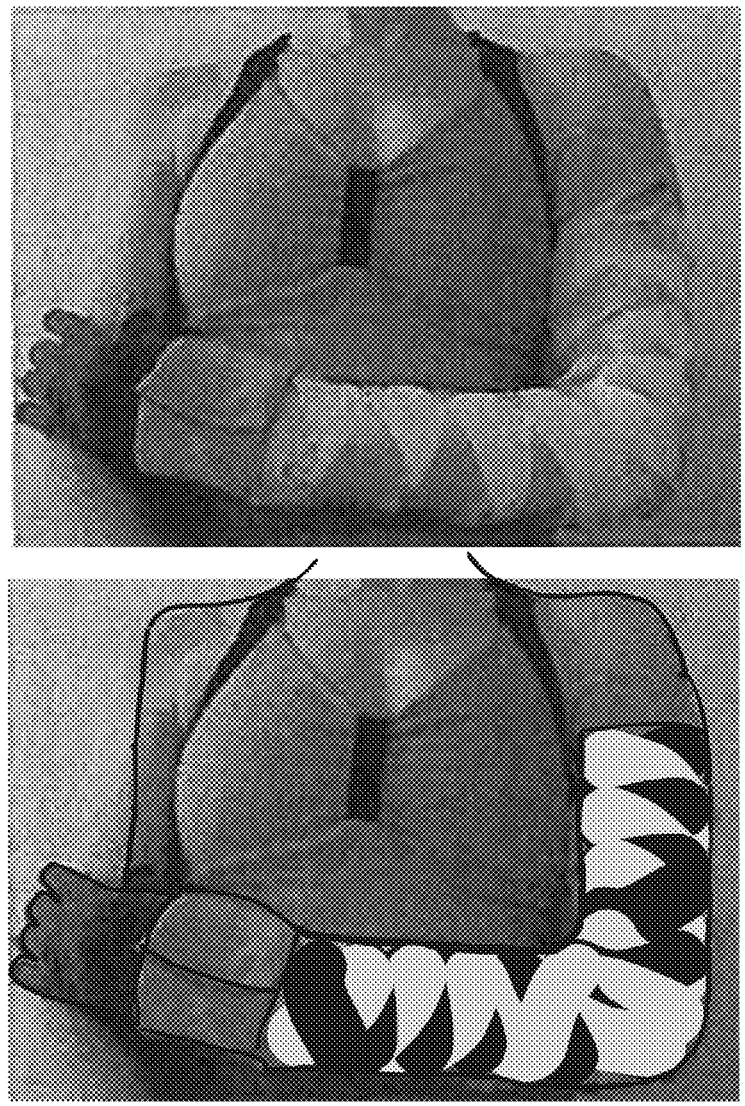
FIG. 1C illustrates a substrate for supporting an arm/shoulder according to another form of the present invention.
Figure 2:
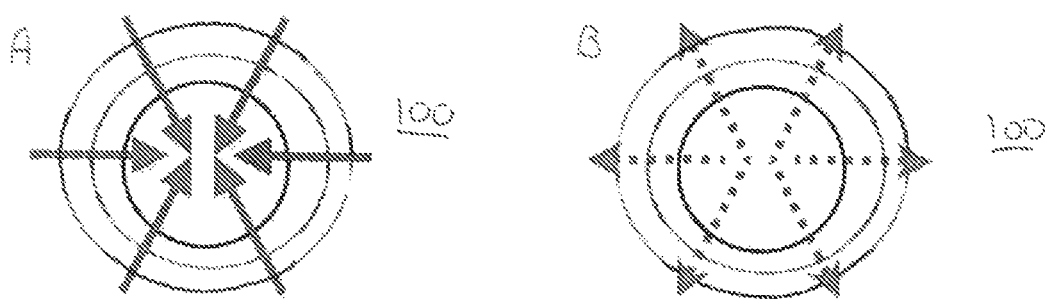
FIG. 2A illustrates circumferential constriction of the substrate of FIGS. 1A-C when the substrate is extended.
FIG. 2B illustrates circumferential expansion of the substrate of FIGS. 1A-C when the extension force on the substrate ceases.

The substrate may also be in the form of a compression stocking as illustrated in FIG. 1B.

The use of threads having varying composition along their length also imparts spatially-controlled elasticity to substrate 16, whereby different regions of the substrate have different temporally-controlled elasticity. The fibrils and, consequently, the threads have different elasticity, stiffness, thinning and swelling properties.

The substrate 16 transitions between a first state and a second state when activated by applying a force to the substrate. The transition is achieved by the substrate storing and converting the potential energy obtained from the force to mechanical pressure and/or kinetic energy over time.

Stretching the substrate 16 causes a corresponding transversal reaction on the substrate. For example, applying an axial force (i.e. stretching the substrate length-wise) to the substrate of FIG. 1A would cause a circumferential contraction.

In order to control the behaviour of the substrate in response to a force applied to the substrate, a multi-layered substrate is provided, with each layer having a different stiffness. For example, the multi-layered substrate may have increasing or decreasing stiffness in the radial direction.

In FIGS. 2A and 2B, a length-wise (i.e. axial) stretch of the substrate 100 causes a circumferential contraction of the substrate, while releasing the stretching force causes a circumferential expansion of the substrate.

Figure 3:
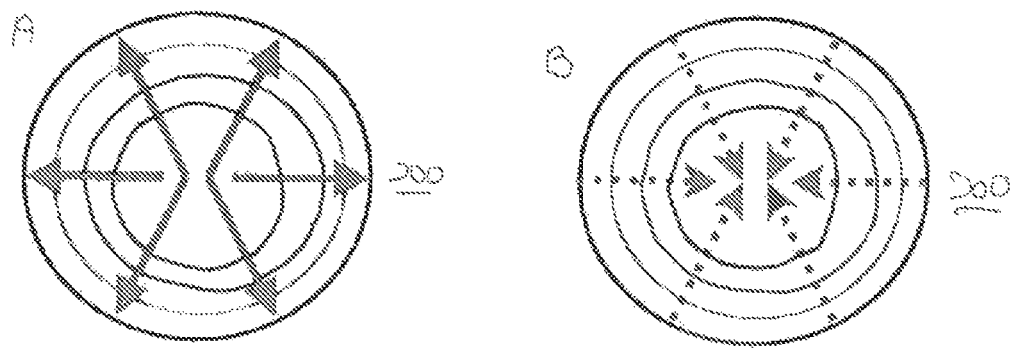
FIG. 3A illustrates circumferential expansion of the substrate of FIGS. 1A-C when the substrate is extended.
FIG. 3B illustrates circumferential constriction of the substrate of FIGS. 1A-C when the extension force on the substrate ceases.

Alternatively, in FIGS. 3A and 3B, a length-wise (i.e. axial) stretch of the substrate 200 causes a circumferential expansion of the substrate, while a release of the stretch causes a circumferential contraction of the substrate.

Referring to FIG. 1A, in the second state, the substrate supports and exerts a pressure on the body part. As the substrate transitions from the second state to the first state, the substrate generates a dynamic pressure gradient, in the form of peristaltic movements, to the arm (see arrows on FIG. 1A). This may be used to improve blood circulation within the arm or simply used to apply pressure to the arm. The pressure on the arm is substantially reduced or removed when the substrate is in the first state.

Figure 4:
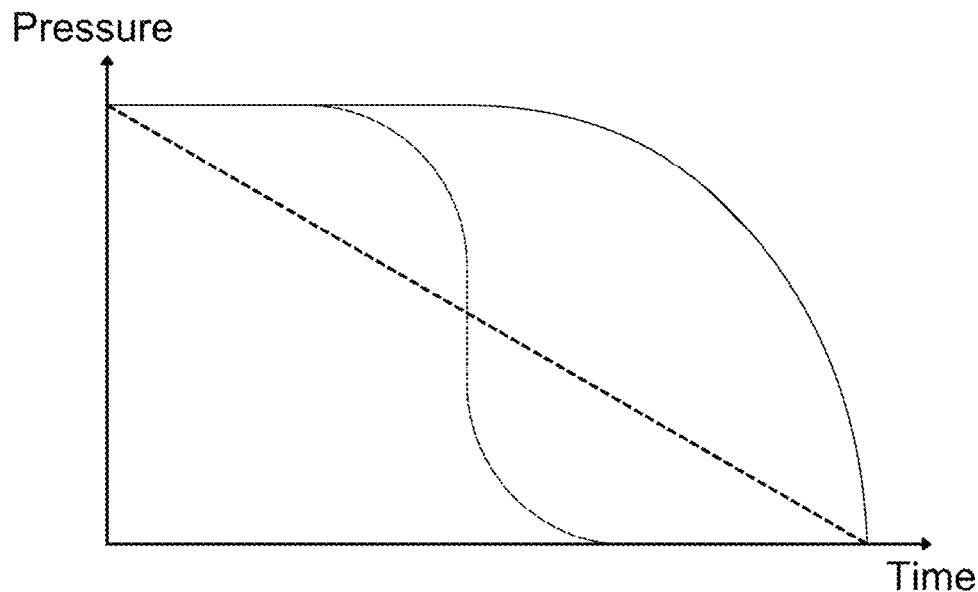
FIG. 4 illustrates the different pressure gradient profiles of a substrate of FIGS. 1A-C.

The pressure gradient during the transition from the second state to the first state may be any one or a combination of constant, increasing or decreasing gradients (see FIG. 4 for representation profiles).

As such, the substrate allows targeted harnessing or transfer of displacements of the arm to induce a change in the substrate structure.

Figure 5:
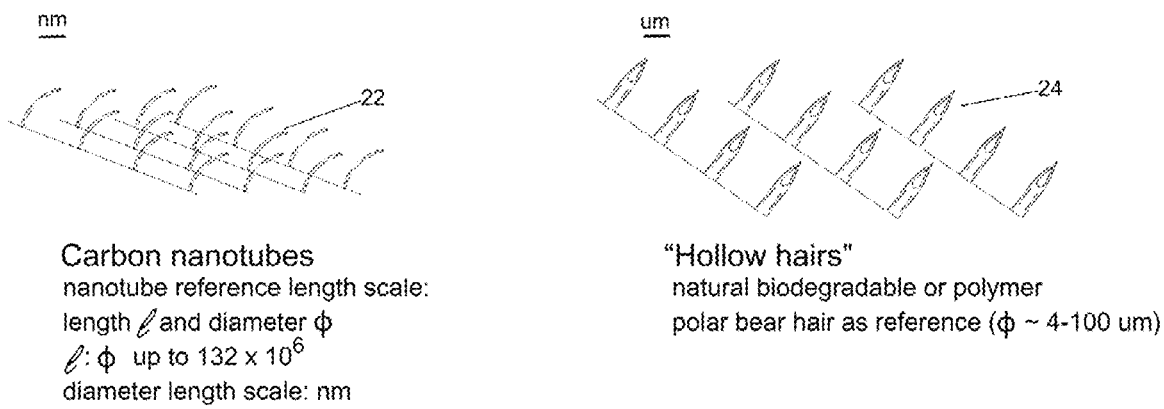
FIG. 5 illustrates various connectors of the substrate of FIGS. 1A-C for attaching to a body part.
Figure 5:
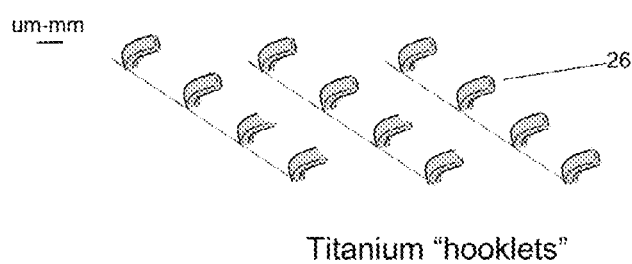

In another form of the invention, the substrate includes a plurality of connectors for providing a non-permanent grip onto a body part (see FIG. 5). The connectors include, among others, carbon nanotubes 22, hollow hairs 24 or titanium hooklets 26.

The plurality of connectors provides multiple non-permanent attachment points for connecting the substrate to a surface of a body part.

Movement of the body part may result in excessive force being exerted on the attachment points. In order to prevent these forces from damaging the body part, some connectors detach from the body part when a predetermined force magnitude and/or direction is exceeded during the movement. Conversely, some connectors may attach or re-attach to the body part below the predetermined force magnitude and/or opposite to the predetermined direction. Suitably, some connectors attach or re-attach to the body part during movement of the body part.

This provides a more constant gripping force between the substrate and the body part compared to fixed connectors such as sutures or clamps.

Advantageously, when the connector is an internal fixation or an external support device, the connectors effectively protect surrounding body parts up to and beyond the failure load or strain. This is because the process of detachment absorbs energy. In this respect, typically, a body part is damaged when it detaches from permanent connectors (through energy absorption that causes tearing). However, in the present invention, the energy is dissipated during the detachment process which allows the body part to be reconnected to the substrate without damage.

In use, the substrate 10 is worn over an arm of the user and the collar portion 14 secured to the neck of the user via closure 28, in the form of a hook and loop fastener. This places the substrate 10 in the first state (FIG. 6A).

Figure 6:
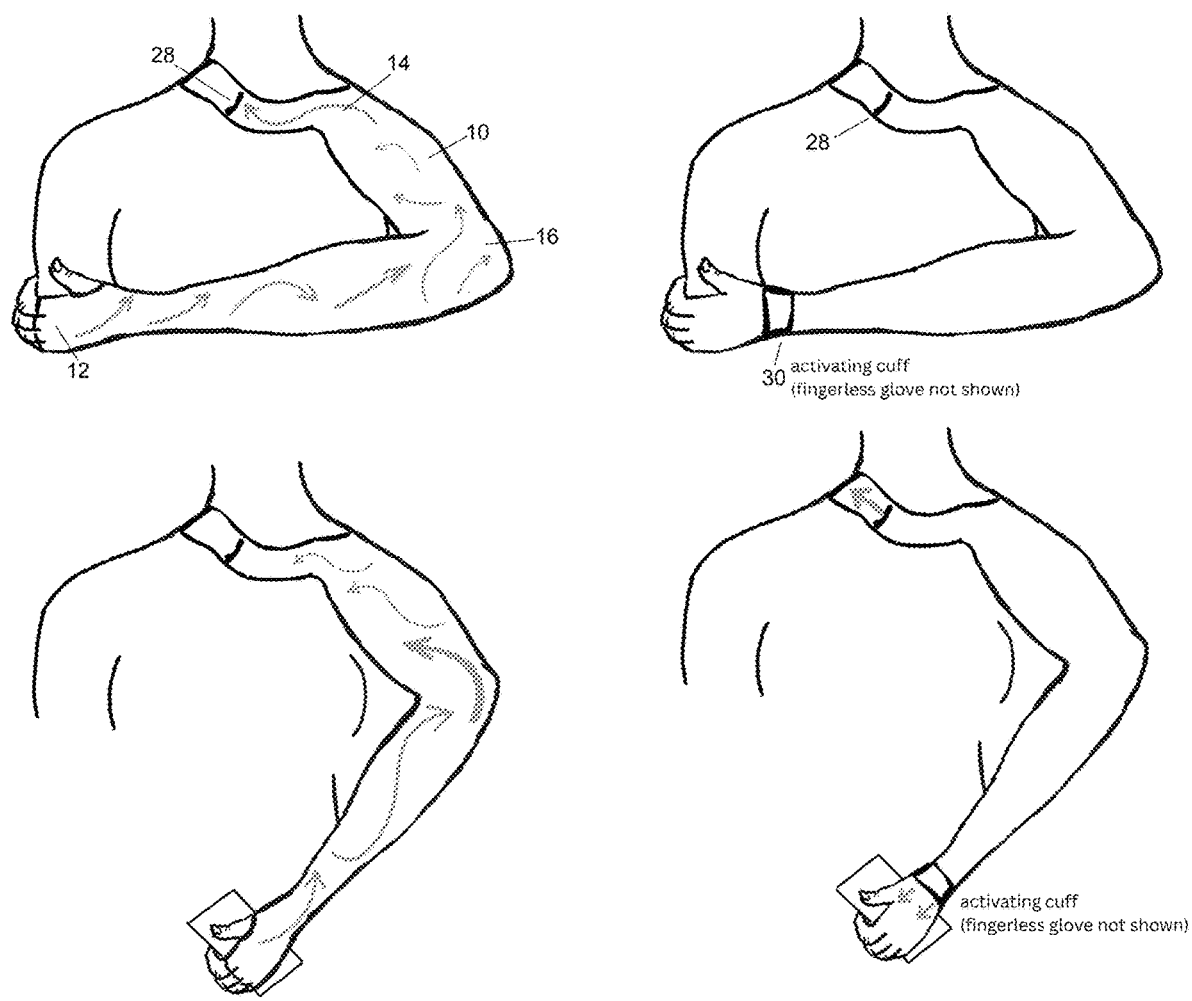
FIG. 6 is a schematic illustrating the steps for operating the substrate of FIG. 1A or 1C.

In order to move the substrate 10 into the second state, the user folds back the fingerless gloves 12 to expose the activating cuff 30 and tightens the neck portion using closure 28 (FIG. 6B). The arm of the user is then extended and the activating cuff is stretched to allow the user to re-engage the fingerless glove 12 (FIG. 6C). This action causes a circumferential contraction of the substrate 10 around the arm.

Over time, as the substrate transitions from the second state to the first state, a dynamic pressure gradient, in the form of peristaltic movements, are transmitted to the arm (FIG. 6D). Once the substrate returns to the first state, the steps are repeated to return the substrate to the second state and maintain pressure on the arm.

Accordingly, there is provided a substrate that can be applied to and maintain pressure on a body part, and reduce damage to the body part.

The invention claimed is:

1. A woven substrate that can be applied to a user's body part comprising:
    a plurality of woven threads that form the woven substrate, the woven substrate including a region of temporally-controlled elasticity that varies over time and transitions between a first state and a second state when activated, wherein the first state is more relaxed than the second state, and the region of the woven substrate can at least partially revert from the second state to the first state over an extended time period resulting from the temporally-controlled elasticity of the region of the woven substrate, and
    wherein the region of the woven substrate is configured to apply a treatment/mechanical force to the body part as the region of the woven substrate transitions from the second state to the first state, and wherein the treatment/mechanical force is a function of the temporally controlled elasticity of the region of the woven substrate, and
    wherein the temporally controlled elasticity is provided by a weave pattern of the woven threads and/or elasticity of the woven threads that varies along lengths and/or within cross-sections of the woven threads.

2. The substrate according to claim 1, wherein the substrate includes a plurality of connectors for attaching the substrate to a body part, tissue, or another substrate to reduce relative movement of the substrate to the body part tissue, or another substrate.

3. The substrate according to claim 2, wherein the plurality of connectors are projections which provide a grip that has a predetermined detachment load and/or direction to hold the substrate and to minimize damage to the body part.

4. The substrate according to claim 2, wherein the connectors are hollow to deliver biologic and/or pharmaceutical agents and/or establish conduits between the connector and a body part.

5. The substrate according to claim 1, wherein internal energy of the substrate in the first state is less than internal energy of the substrate in the second state.

6. The substrate according to claim 1, wherein the force applied to the body part by the substrate varies as the substrate reverts from the second state to the first state.

7. The substrate according to claim 1, wherein different regions of the substrate possess different temporally-controlled elasticity.

8. The substrate according to claim 1, wherein the substrate moves from the second state to the first state via any one of elongation or shortening of the substrate, or relaxation or stiffening of the substrate.

9. The substrate according to claim 1, wherein the substrate possesses spatially-controlled elasticity, whereby different regions of the substrate have different elasticity.

10. The substrate according to claim 1, wherein the substrate is woven using at least two threads having different elasticity.

11. The substrate according to claim 1, wherein the substrate includes at least one thread possessing elasticity that varies along the length of the thread.

12. The substrate according to claim 1, wherein the substrate includes at least one thread possessing elasticity that varies within the cross-section of the thread.

13. The substrate according to claim 1, wherein the substrate is woven using threads arranged in different directions such that the threads move frictionally relative to one another causing the transition from the fast state to the second state to occur over an extended time period.

14. The substrate according claim 1, wherein the connectors are oriented in more than one direction to provide a multi-directional grip onto the body part to reduce the likelihood of the substrate detaching from the body part when subjected to a force.

15. The substrate according to claim 1, wherein the substrate comprises sub-weave bands in biaxial weave structure.

16. The substrate according to claim 1, wherein the substrate is anisotropic.

17. The substrate according to claim 1, wherein the substrate is a biaxial braided sleeve whose circumference constricts with an increase in length of the sleeve.

18. The substrate according to claim 1, wherein the substrate comprises a degradable material.

19. A sleeve for fitting over a body part comprising:
a plurality of woven threads that form a woven substrate, the woven substrate including at least one region of temporally-controlled elasticity that varies over time, wherein the region of the woven substrate is transitionable between a first state and a second state by movement of the body part covered by the sleeve over an extended time period resulting from the temporally-controlled elasticity of the region of the woven substrate, and wherein the region of the woven substrate is configured to apply a treatment/mechanical force to the body part, as the region of the woven substrate transitions from the second state to the first state, and wherein the treatment/mechanical force is a function of the temporally controlled elasticity of the region of the woven substrate, and wherein the temporally controlled elasticity is provided by a weave pattern of the woven threads and/or elasticity of the woven threads that varies along lengths and/or within cross-sections of the woven threads.

20. The sleeve according to claim 19, wherein the sleeve comprises multiple layers of the substrate, wherein each substrate has different temporally-controlled elasticity.

* * * * *